United States Patent [19]

Lomholt

[11] Patent Number: 5,255,670
[45] Date of Patent: Oct. 26, 1993

[54] AIR RESERVOIR

[76] Inventor: Vagn N. F. Lomholt, Lundevej 4, Allerod, Denmark, 3450

[21] Appl. No.: 910,082
[22] PCT Filed: Jan. 14, 1991
[86] PCT No.: PCT/DK91/00011
   § 371 Date: Jul. 6, 1992
   § 102(e) Date: Jul. 6, 1992
[87] PCT Pub. No.: WO91/10465
   PCT Pub. Date: Jul. 25, 1991

[30] Foreign Application Priority Data

Jan. 15, 1990 [DK] Denmark ................ 0115/90

[51] Int. Cl.⁵ ........................................ A61M 16/04
[52] U.S. Cl. .......................... 128/200.24; 128/207.15;
                                     128/912; 73/731
[58] Field of Search .......... 128/207.15, 200.24,
   128/205.23, 207.14, 911, 912; 73/700, 715, 729,
                                     730, 731; 604/100

[56] References Cited

U.S. PATENT DOCUMENTS

| | | | |
|---|---|---|---|
| 2,417,449 | 3/1947 | Rubin | 73/731 X |
| 3,241,514 | 3/1966 | Grimland | 73/731 X |
| 3,347,222 | 10/1967 | Kohrer | 128/205.23 X |
| 3,642,005 | 2/1972 | McGinnis | 128/207.15 |
| 3,848,605 | 11/1974 | Harautuneian et al. | 128/207.15 |
| 3,890,967 | 6/1975 | Elam | 128/205.23 X |
| 3,898,987 | 8/1975 | Elam | 128/205.23 |
| 3,980,082 | 9/1976 | Miller | 73/731 X |
| 4,286,603 | 9/1981 | Marshall | 73/731 X |
| 4,592,747 | 6/1986 | Pool | 604/246 |
| 5,060,520 | 10/1991 | Strasser | 73/715 |

FOREIGN PATENT DOCUMENTS

| | | | |
|---|---|---|---|
| 1473497 | 5/1969 | Fed. Rep. of Germany | 73/700 |
| 2-28533 | 9/1990 | Japan | 73/700 |
| 1464271 | 2/1977 | United Kingdom . | |
| 2164565 | 3/1986 | United Kingdom . | |

Primary Examiner—Edgar S. Burr
Assistant Examiner—Eric P. Raciti
Attorney, Agent, or Firm—Merchant & Gould, Smith, Edell, Welter & Schmidt

[57] ABSTRACT

An air reservoir (4) intended for regulating the pressure in the sealing cuff of a respiration catheter has a wall consisting of an elastic membrane (3). The reservoir also functions as a pressure gauge, the elastic membrane when inflated being caused to contact a semitransparent plate (2) which is firmly connected with a rigid part (1) of the reservoir. At contact between the membrane and the plate, indicator rings on the membrane become visible through the semitransparent plate.

5 Claims, 1 Drawing Sheet

AIR RESERVOIR

The invention concerns an air reservoir of the type stated in the introductory portion of claim 1.

Endotracheal tubes for insertion through the mouth, the nose or implanted in the neck (oro-naso and tracheostomy tubes) are usually provided with an inflatable cuff for sealing against the tracheal wall. The efficiency of the sealing is determined by the magnitude of the cuff pressure against the tracheal wall since the inflated cuff does not seal off pressures exceeding the pressure of the cuff against the wall. The air pressure in the cuff determines the pressure against the tracheal wall. The pressure of the cuff against the tracheal wall can be controlled and regulated only if the cuff has a sufficiently large diameter to make contact with the tracheal wall without any stretching of the sheet material of the cuff, i.e. the cuff must be lying folded on the tracheal wall. If this demand is met, the pressure in the cuff is identical with its pressure on the wall.

If the pressure of the cuff against the tracheal wall is considerably higher than 30 cm $H_2O$ the blood supply to the mucosa is occluded, and this causes damage in the form of superficial or deeper ulcerations after some time. This damage is prevented in that the sealing cuff, lying folded on the wall, is kept inflated from an outer pressure source with a constant, regulated pressure of 20 to 30 cm $H_2O$.

The sealing cuff has the additional function of preventing liquid (blood, saliva, vomit) from flowing past the cuff down into the lungs. It has been found that this function is accomplished when the pressure of the sealing cuff against the tracheal wall is at least 20 to 30 cm $H_2O$.

Spontaneous changes in the diameter of the trachea, changes in the catheter position and the diffusion of certain anaesthetic gases through the wall of the sealing cuff may cause considerable changes in the pressure in the sealing cuff if the inflation pressure is not controlled and regulated.

A reservoir of the present type is capable of maintaining the pressure within the stated pressure range in the sealing cuff of a respiration catheter as the reservoir compensates for the rise and fall in pressure that might occur in the sealing cuff.

The object of the invention is to provide a reservoir of the present type which has means for indicating the magnitude of the pressure in the reservoir.

This object is obtained in that the reservoir is constructed as stated in the characterizing portion of claim 1 since, in this structure, the externally observable size of the engagement face between the membrane and the plate depends upon and is thus a measure of the pressure in the reservoir.

Preferably the membrane is diffusion proof as stated in the claims. The feature protects the reservoir against diffusion through the membrane and consequent changes in pressure. One embodiment of the invention makes it possible to relate the size of the engagement face to predetermined values indicated by the markings.

DETAILED DESCRIPTION

Figure 1:
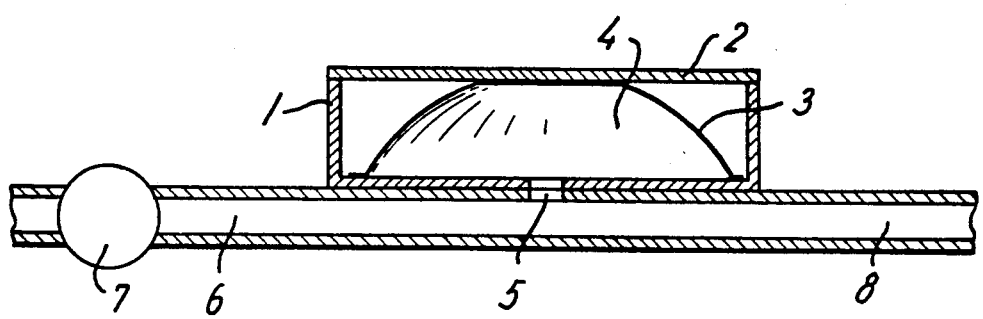
FIG. 1 is a side view shown in section.

An embodiment of the air reservoir is shown schematically in the drawing, partly in longitudinal section, FIG. 1 partly seen from above, FIG. 2, and will be described more fully below with reference to the drawing.

In the drawing, 1 is a circular, inelastic container, the edge of an elastic, diffusionproof membrane 3 being fastened along the bottom edge of said container. The container has as supply tube 6 for filling with air and a cut-off valve 7. Through an opening 5, the air supply tube communicates with a reservoir 4 formed by the elastic membrane 3 and the bottom of the container 1. The reservoir communicates with the sealing cuff of an endotracheal tube (not shown) via a supply tube 8. The container 1 is covered by a lid 2, whose underside has such a roughness that the cover is semitransparent. The upper side of the membrane 3 is wetted with a thin liquid layer, e..g. silicone oil, and is imprinted with one or more marker-or indicator rings 9.

When the reservoir 4 is filled with air, the elastic membrane 3 is stretched and consequently brought into contact with the underside of the lid. The liquid is hereby caused to fill the small cavities in the rough underside of the layer so that the lid will be transparent, and one or more indicator rings 9 are visiable through the semitransparent lid and thereby indicate the air pressure in the reservoir.

Figure 2:
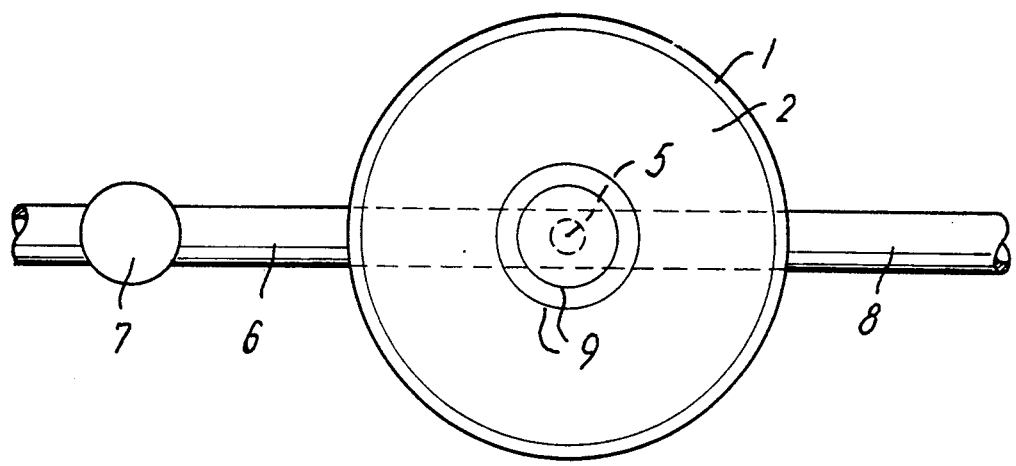
FIG. 2 is a top view of the invention.

The lid does not have to be flat, as shown in FIG. 1, but may be outwardly vaulted, which increases the volume of the reservoir and increases the distances between the indicator rings compared with a flat lid at the same pressure, so that also the pressure reading will be more precise.

Other modifications to the details of the shown and described reservoir are possible within the scope of the invention.

I claim:

1. An air reservoir for control of the pressure in the sealing cuff of a respiration catheter, having a rigid supporting part and a wall consisting of an elastic membrane having an inner side and an outer side whose edges are connected with said rigid supporting part of the reservoir, characterized in that this rigid supporting part is firmly connected with a semitransparent plate so arranged with respect to the membrane that the outer side of the membrane is pressed into engagement with the plate by the pressure in the reservoir, and that a thin liquid layer is provided on the outer side of the membrane, said liquid layer changing the optical properties of the plate from semitransparent to transparent when the membrane engages the plate.

2. A reservoir according to claim 1, characterized in that the membrane is diffusionproof.

3. A reservoir according to claim 1 in that the reservoir is equipped with one or more markings which indicate the size of the pressure upon engagement between the membrane and the plate.

4. A reservoir according to claim 3, characterized in that the marking or markings are ring-shaped.

5. A reservoir according to claim 4, characterized in that the plate is outwardly vaulted.

* * * * *